(12) United States Patent
Reinert, Sr.

(10) Patent No.: US 7,347,103 B2
(45) Date of Patent: Mar. 25, 2008

(54) PILE TESTING REACTION ANCHOR APPARATUS AND METHOD

(76) Inventor: Gary L. Reinert, Sr., 639 North Ave., Pittsburgh, PA (US) 15209

( * ) Notice: Subject to any disclaimer, the term of this patent is extended or adjusted under 35 U.S.C. 154(b) by 113 days.

(21) Appl. No.: 11/266,978

(22) Filed: Nov. 4, 2005

(65) Prior Publication Data

US 2006/0070454 A1 Apr. 6, 2006

Related U.S. Application Data

(60) Continuation of application No. 10/106,538, filed on Mar. 26, 2002, now abandoned, which is a division of application No. 09/440,026, filed on Nov. 12, 1999, now Pat. No. 6,363,776.

(51) Int. Cl.
*G01N 3/08* (2006.01)

(52) U.S. Cl. ...................................... 73/818

(58) Field of Classification Search .................. 73/818
See application file for complete search history.

(56) References Cited

U.S. PATENT DOCUMENTS

| | | | | |
|---|---|---|---|---|
| 3,946,601 A * | 3/1976 | Yizhaki | ........................ | 73/84 |
| 4,344,721 A * | 8/1982 | Goldsmith | ................. | 405/224 |
| 4,648,751 A * | 3/1987 | Coleman | .................... | 405/209 |
| 4,843,785 A | 7/1989 | Sero et al. | .................... | 52/160 |
| 4,882,891 A | 11/1989 | Sero et al. | .................... | 52/742 |
| 4,974,997 A | 12/1990 | Sero et al. | .................. | 405/231 |
| 5,234,290 A | 8/1993 | Collins | ........................ | 405/249 |
| 6,210,077 B1 * | 4/2001 | Kondo | ........................ | 405/244 |
| 6,318,933 B1 * | 11/2001 | De Medeiros et al. | ... | 405/223.1 |
| 6,363,776 B1 * | 4/2002 | Reinert, Sr. | .................... | 73/84 |
| 2002/0095976 A1 * | 7/2002 | Reinert, Sr. | .................... | 73/84 |

OTHER PUBLICATIONS

ASTM D1143-81 "Standard Test Method for Piles Under Static Compressive Load".

* cited by examiner

*Primary Examiner*—Max Noori
(74) *Attorney, Agent, or Firm*—The Webb Firm (57) ABSTRACT

Pile testing apparatus and method apply static compressive forces on a pile to be tested for load bearing capacity. Retractable and reusable reaction anchor assemblies are installed into the ground for pile testing and then are retrieved from the ground after completion of the pile testing and are reused from one pile test site to another. The invention operates to receive an equal and opposite reaction force on an I-beam and provide at least two retractable and reusable reaction anchor assemblies installed into the ground at a depth significantly less than required with conventional pile testing methods. The I-beam is braced by the two retractable and reusable reaction anchor assemblies and held stationary in counter-action against the opposite reaction force on the I-beam. The pile testing apparatus and method of the present invention reduce costs considerably and can be used immediately as contrasted to conventional methods using concrete.

15 Claims, 7 Drawing Sheets

PILE TESTING REACTION ANCHOR APPARATUS AND METHOD

This patent application is a Continuation of prior, U.S. patent application Ser. No.: 10/106,538 filed Mar. 26, 2002, now abandoned which is a Divisional of prior, U.S. Pat. application Ser. No.: 09/440,026, filed Nov. 12, 1999, now U.S. Pat. No. 6,363,776.

BACKGROUND OF THE INVENTION

1. Technical Field

This invention relates to an apparatus and method for testing load bearing capacity on a pile or group of piles. In one aspect, this invention relates to novel apparatus and method for testing load bearing capacity on a pile or group of piles, utilizing a reaction anchor apparatus and method.

2. Background

In the construction industry, various types and shapes of piles are utilized for constructing foundations on the piles. These foundations are the structural supports upon which many types of constructions are built. Foundations support the loads imposed upon them and, hence, the loads imposed upon the piles, by such constructions as high rise buildings, power plants, river dams, and many other constructions.

Among the most common types and shapes of piles are timber piles, steel pipe piles, H-Piles, L-Piles, precast concrete piles, and cast-in-place concrete piles. These piles are installed vertically or battered at an angle.

Piles are forced deep down into the soil by repetitive blows on their tops. These powerful blows are provided by pile-driving machines, also known as hydraulic hammers. Piles also can be poured-in, i.e., cast-in-place, by drilling a deep hole in the soil, then filling it with concrete. Generally, reinforcement steel rods, also known as rebar, are introduced into the hole prior to filling it with concrete.

The most commonly used method of installation of piles is by beating them down into the ground by means of a pile-driving machine.

Through the years, the construction industry has developed apparatus and testing methods for determining the capability of a vertical pile, a batter pile, or a group of piles to resist a required level of static compression loads as actually applied on the pile or group of piles. These testing methods determine whether a pile or group of piles has adequate bearing capacity or not.

Testing methods have been standardized by the American Society for testing materials, also known as ASTM. The Standard Test Method For Piles Under Static Axial Compressive Load, designation D1143-81, (reapproved 1987) covers pile testing utilizing conventional apparatus and methods for determining the capability of piles to resist a static compression load as actually applied on the piles.

INTRODUCTION TO THE INVENTION

According to ASTM D1143-81, single piles must be tested to 200% of the anticipated design load, while pile groups must be tested to 150% of the group design load.

Conventionally, for testing an individual pile, two additional piles have to be installed, using the same method and equipment utilized for installing the pile under test. These additional piles are driven into the soil on two diametrically opposing sides of the pile to be tested and at not less than seven feet from the pile being tested. These additional piles are known in the trade as anchor piles.

A test beam then is installed across the tops of the anchor piles, tying them to the beam and above the pile under test, forming what is known in the trade as a reaction frame. This test beam is set on a hydraulic jack, which in turn is set on top of the pile under test.

Upward hydraulic push is applied by the jack against the beam. The beam cannot move up because it is tied onto the anchor piles. As a result, the hydraulic power, i.e., the force exerted by the hydraulic jack, is applied downwardly against the top of the pile under test. These forces are applied incrementally, increasing at pre-established time intervals and held then at the maximum predetermined test loading for a specified length of time.

Certain instrumentation is utilized for determining the axial loading and for determining any movements, e.g., axial, rotational, and lateral, of the pile under test.

If the test proves the capability of the pile to resist the specified axially applied compressive loading, and if there are no other deviations beyond acceptable standards, then that pile is determined to be fit to be used for its intended purposes, i.e., it has adequate bearing capacity.

Testing a group of piles instead of a single pile utilizes the same procedure, but in the case of a group of piles, the various piles in the group are capped by a common cap, and the test load is applied uniformly upon the pile cap. Pile caps generally are poured, reinforced concrete slabs, specifically engineered for that purpose. A larger number of anchor pile pairs is required when testing pile groups.

After the test, anchor piles are left in place, after sawing off their tops, i.e., after sawing-off the top portion of the pile protruding above ground. It is extremely difficult and expensive to pull those anchor piles out of the ground.

Utilizing anchor piles for testing an installed pile or a group of piles presents several drawbacks.

One drawback of the conventional pile testing apparatus and methods is the large installation cost of driving into the soil one, two, or more pairs of anchor piles per each single pile or group of piles to be tested.

Another drawback of the conventional pile testings is the difficulty in handling the long and heavy anchor piles required for the testings, e.g., requiring a tractor and a trailer for their transportation, requiring a special crane for lifting in or out of the trailer, requiring an expensive, cumbersome pile driving machine for driving the anchor piles into the ground.

Another drawback of the conventional pile testings is the difficulty of setting the long and heavy anchor piles in a vertical position for driving them into the ground.

Yet another drawback of the conventional pile testings is the loss of the anchor piles, because after the test is completed, they are not reusable in future tests, and therefore, their top ends protruding above the ground have to be sawed off, abandoning the pile in the ground.

It is an object of the present invention to provide anchoring apparatus and installation methods which substantially reduce the cost of testing piles or group of piles.

Another object of the present invention is to provide anchoring apparatus and methods which simplify the pile testing process.

Yet another object of the present invention is to provide anchoring apparatus and methods for the testing of piles which simplify transportation and eliminate utilizing a tractor and a trailer.

Still another object of the present invention is to provide anchoring apparatus and methods for the testing of piles which do not require the use of a pile driving machine.

Another object of the present invention is to provide anchoring apparatus and methods for the testing of piles which do not require the use of anchor piles for the pile testing process.

Yet another object of the present invention is to provide anchoring apparatus and methods for the testing of piles which are reusable.

These and other objects of the present invention will become apparent from a careful review of the detailed description and the figures of the drawings, which follow.

SUMMARY OF THE INVENTION

The apparatus and method of the present invention provide novel means and method for testing piles for load bearing capacity. The novel means and method of the present invention include applying a static compressive force on a pile or group of piles to be tested for load bearing capacity, receiving an equal and opposite reaction force on an I-beam, providing at least two reaction anchor assemblies on opposite sides of the pile, and bracing the I-beam by the two reaction anchor assemblies to hold the I-beam stationary in counter-action against the opposite reaction force on the I-beam. In one aspect, each reaction anchor assembly has an anchoring head, a pipe column, a center, a pulling rod passing through the center, a pair of swingable anchoring plates and preferably two pairs of swingable anchoring plates, and a frusto-cone for pivoting the swingable anchoring plates. In one aspect, the pipe column has four fins welded longitudinally along the pipe column. In one aspect, the reaction anchor assembly is preassembled for transportation to a pile test site. The novel means and method for testing piles provide for retrieving the reaction anchor assemblies from the ground after completion of the pile test and reusing the reaction anchor assemblies from one pile test site to another.

BRIEF DESCRIPTION OF THE DRAWINGS

FIG. 3 also shows some measuring instruments.

FIG. 5 shows a hydraulic assembly utilized for anchoring the reaction anchor and support assembly, also in accordance with the apparatus and methods of the present invention.

FIG. 8 shows a centering and support plate lifted up from the box.

FIG. 9 also shows some measuring instruments.

DETAILED DESCRIPTION

Figure 1:
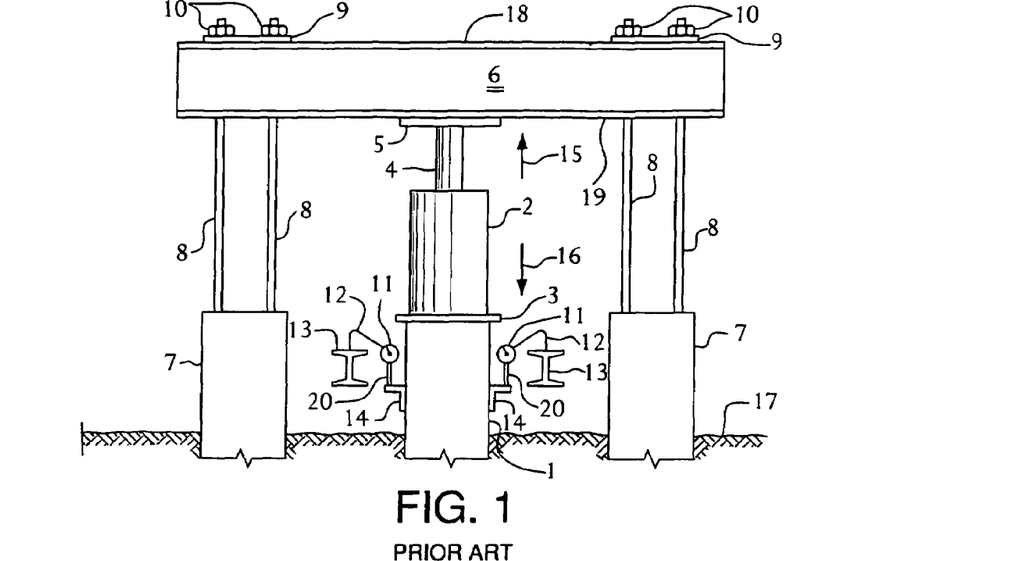
FIG. 1 is an elevation view showing the single pile testing apparatus of the existing art.
Figure 2:
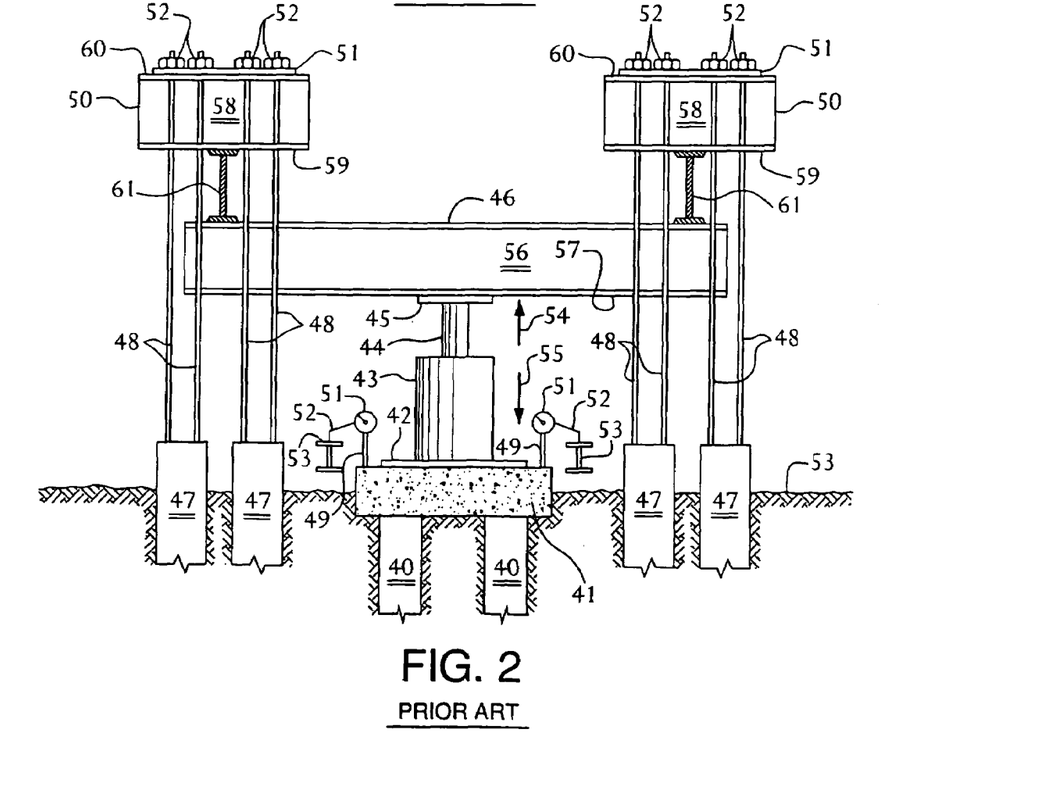
FIG. 2 is an elevation view showing the pile group testing apparatus of the existing art.

FIG. 1 and FIG. 2 depict apparatus and method representing the conventional testing apparatus and method for testing vertical piles, as shown on ASTM D1143-81(reapproved 1987). FIG. 1 depicts the conventional testing apparatus and method for testing a single pile. FIG. 2 depicts the conventional testing apparatus and method for testing a group of piles.

Referring now to FIG. 1, a single pile 1 is shown as having been driven into soil 17. A pair of anchor piles 7 also have been driven into soil 17, at a distance at least seven feet away from or clear of pile 1, i.e., away from the pile 1 under test. A bottom flange 19 of a test beam 6 is set on top of a bearing plate 5 of a piston ram 4 of a hydraulic cylinder 2. The hydraulic cylinder 2 is set on a test plate 3, which is centered on top of the individual pile 1, i.e., the single pile 1.

The test beam 6 is tied to the anchor piles 7 by means of a series of connecting rods 8, a pair of plates 9 on a top flange 18 of the beam 6, and the connecting rods 8 are secured by a series of threaded nuts 10, threaded down against the plates 9.

By the conventional method, a powerful, upwardly driven push is provided by the piston ram 4 of the hydraulic cylinder 2, as represented by an arrow 15. This upwardly driven push is exerted upon the test beam 6, by means of a bearing plate 5, which bears on the bottom flange 19 of the beam 6. The beam 6 is fixedly connected to the anchor piles 7 by means of the threaded nuts 10, tightened on the connecting rods 8, against the plates 9. As a result, the beam 6 cannot move up. The forceful push of the pistons 4 is effectively resisted by the anchor piles 7 because of the friction between the anchor piles 7 and the soil 17. An equivalent forceful push therefore is exerted downwardly on the test plate 3 and, as a result, on the individual pile 1.

Accordingly to ASTM D1143-81(reapproved 1987), the load applied upon the pile 1, which is the pile under test, must be 200% of the anticipated individual pile 1 design load.

The scope of purpose for testing piles is to determine if the pile has adequate bearing capacity, by measuring the response of the pile, e.g., the pile 1, to a static, compressive load, axially applied, as shown by an arrow 16 of FIG. 1.

In addition, pile testings also are utilized for measuring pile movements under axial loading. FIG. 1 shows a pair of dial gages 11, connected by means of a pair of stems 20 to the pile 1, at a pair of lugs 14 and to a pair of reference beams 13 by means of a pair of supports 12.

Referring now to FIG. 2, the conventional testing apparatus and method for a group of piles 40 is represented. Pile group 40 includes, by the way of an example, the two piles 40 which have been driven into a soil 53. A series of anchor piles 47 also have been driven into the soil 53 at a distance at least seven feet away from or clear of any pile 40, i.e., the pile 40 of the pile group under test. A bottom flange 57 of a test beam 56 is set on top of a bearing plate 45 of a ram 44 of a hydraulic cylinder 43. The hydraulic cylinder 43 is set on a test plate 42, which in turn is set on a pile cap 41. The pile cap 41 is centered on top of pile group 40. The pile cap 41 is constructed of reinforced concrete, which is engineered to bear the anticipated load.

The test beam 56 has a pair of beams 61 on its top flange 46. A pair of beams 58 are set with their bottom flanges 59 on top of the I-beams 61. This I-beam set up is all tied down to the anchor piles 47 by means of a series of connecting rods 48 and threaded nuts 52, with a plate 51 on top of each flange 60. The threaded nuts 52 are tightened down against the plates 51.

By the conventional method, a powerful, upwardly driven push is provided by the piston 44 of the hydraulic cylinder 43, as represented by an arrow 54. This upwardly driven push is exerted upon the test beam 56 by means of the bearing plate 45, which bears on the bottom flange 57 of the beam 56. The beam 56 is fixedly connected to the anchor piles 47 by means of the threaded nuts 52 tightened on the connecting rods 48, against the plates 51. As a result, the beam 56 cannot move up. The forceful push of the piston 44 is effectively resisted by the anchor piles 47 because of the friction between the piles 47 and the soil 53. An equivalent, forceful push is exerted therefore downwardly upon the test plate 42, the pile cap 41, and the pile group 40, as represented by an arrow 55.

Accordingly to ASTM D1143-81(reapproved 1987), the load applied upon the pile group 40, which is the pile group under test, must be 150% of the anticipated pile group 40 design load.

These ASTM tests are performed to determine if the pile group has adequate bearing capacity by measuring the response of the pile group, e.g., the pile group 40, to a static, compressive load applied axially, as shown in FIG. 2.

The pile group 40 also is tested to determine movements which occur under loading. FIG. 2 shows a pair of dial gages 51 connected by means of a pair of stems 49 to a pile cap 41 and to a pair of reference beams 53 by means of a pair of supports 52.

Figure 3:
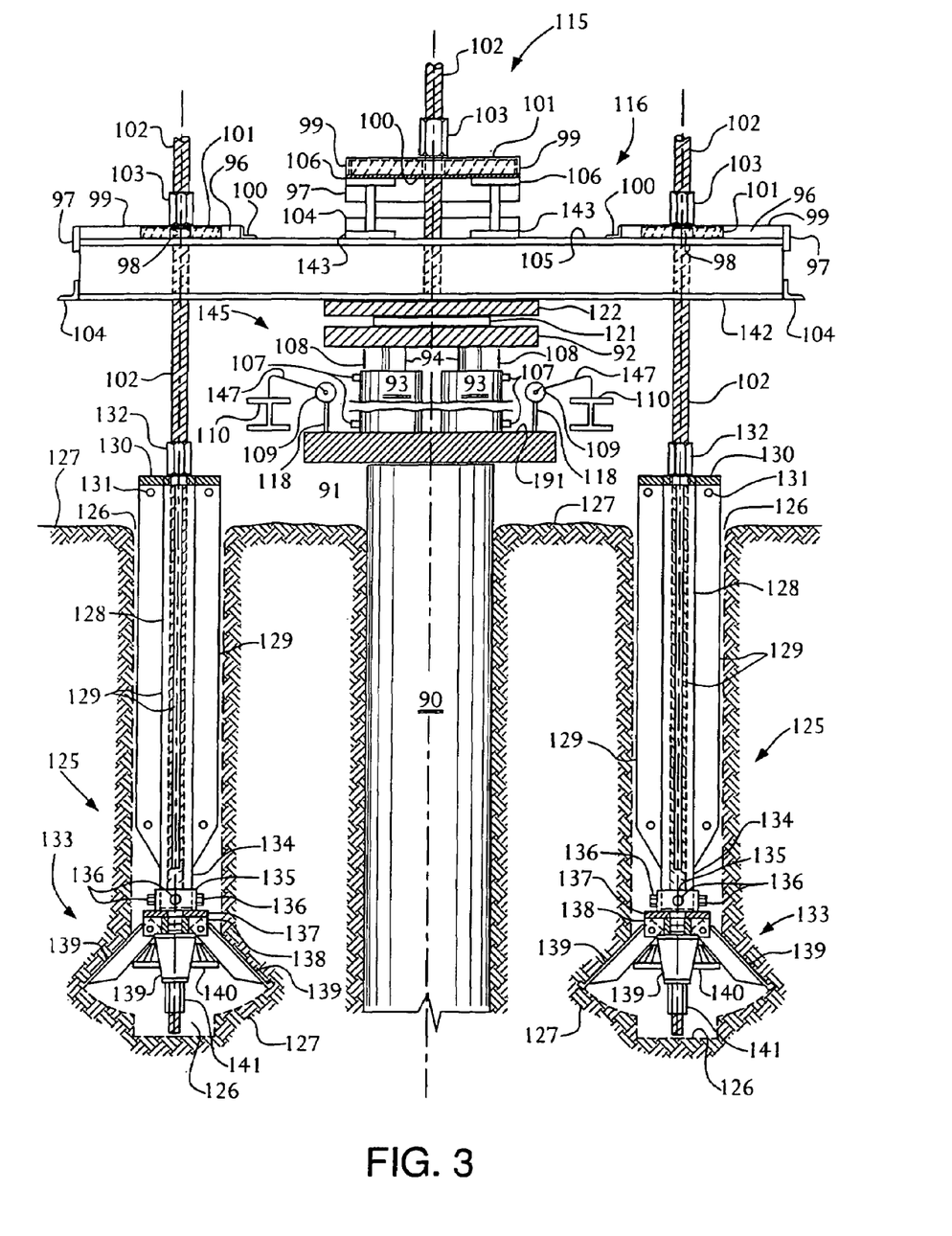
FIG. 3 is an elevation view, partially in section, showing a single pile testing apparatus of the present invention.

Referring now to FIG. 3, a pair of reaction anchor and support assemblies 125 in accordance with the apparatus and the methods of the present invention are shown in the process of testing a single pile 90 under a static, axial load, provided by a hydraulic assembly 145. The reaction anchor and support assemblies 125 provide a point of resistance for a pair of hydraulic cylinders 93 to push against, as the hydraulic cylinders 93 exert a specified testing load on the pile 90, as further described in this detailed description. The reaction anchors and support assemblies 125 are manufactured by SAFE Foundations, Inc., of Pittsburgh, Pa.

Figure 6:
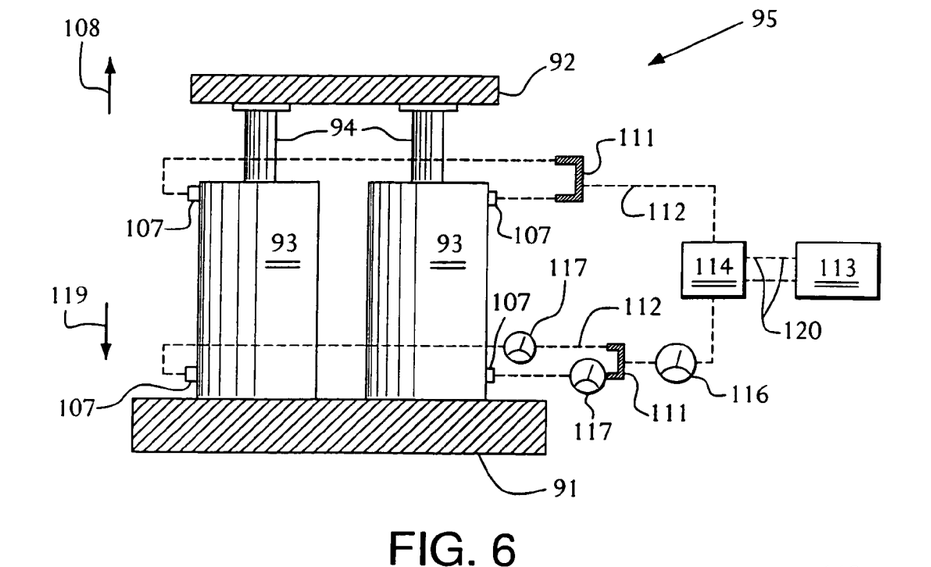
FIG. 6 is a detail view of a hydraulic system component part of the present invention, shown in elevation.

The hydraulic cylinders 93 are set on a bearing plate 91, also known as a test plate 91, with a pair of pistons 94, respectively, upon which a bearing plate 92 is set. The hydraulic assembly could include only a one cylinder and one piston set instead of the pair of cylinders and pistons as shown in FIGS. 3 and 6. A load cell 121 is set between the bearing plate 92 and a bearing plate 122. The bearing plates 91, 92, and 122 are of sufficient thickness to support the test loads provided by the hydraulic assembly 145 without bending, but not less than two inches thick.

The plate 122 bears against a flange 142 of a novel I-beam assembly 116. The I-beam assembly 116 bears against an I-beam assembly 115, which is identical to the beam assembly 116. A pair of flanges 143 of the I-beam assembly 115 are set on top of a pair of flanges 105 of the I-beam assembly 116. The beam assembly 115 is set at ninety degrees of the beam assembly 116 and on top of the beam assembly 116, as shown in FIG. 4, a perspective view, showing some of the elements shown in FIG. 3.

Figure 4:
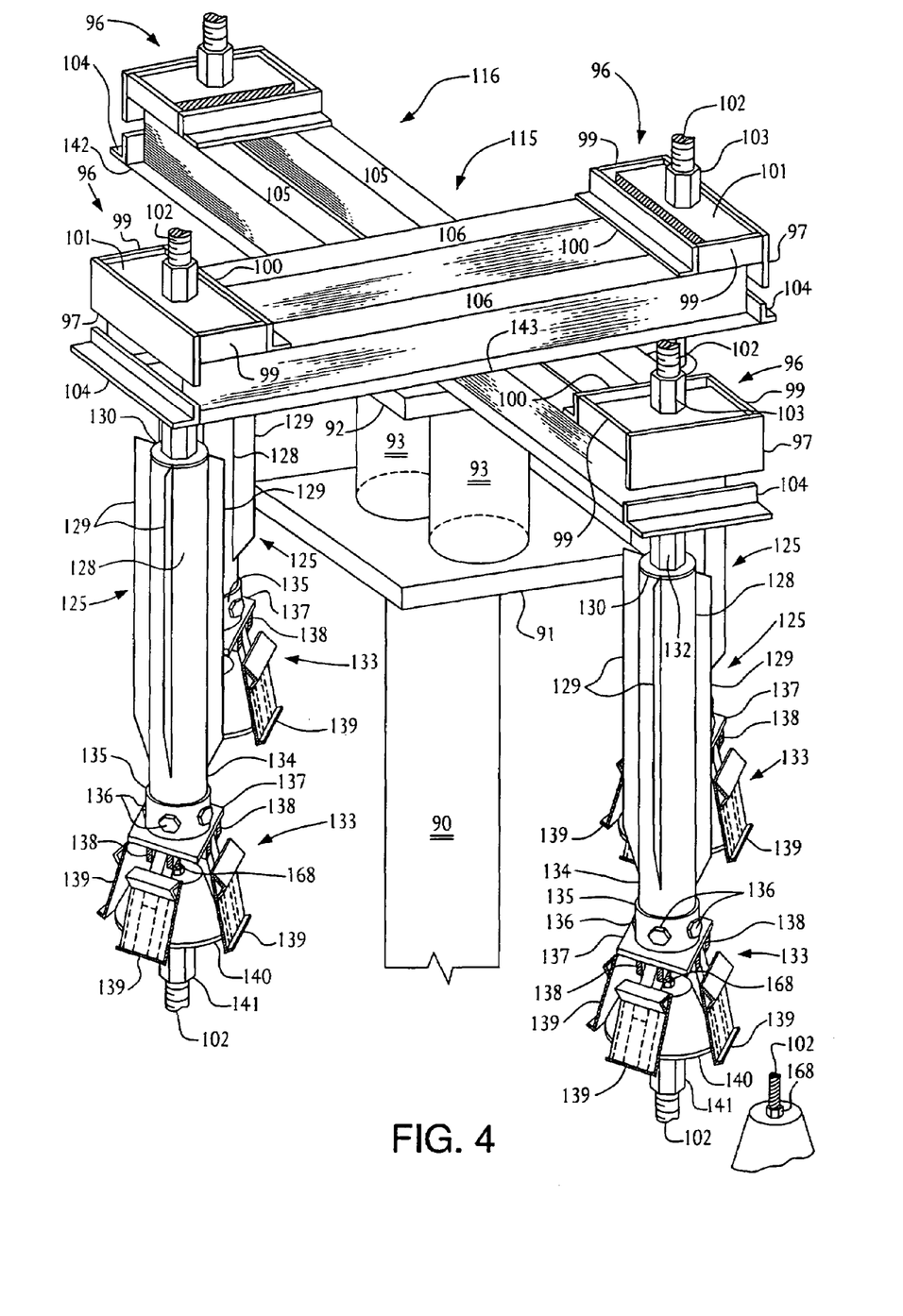
FIG. 4 is a perspective view of FIG. 3 without showing instrumentation.
Figure 8:
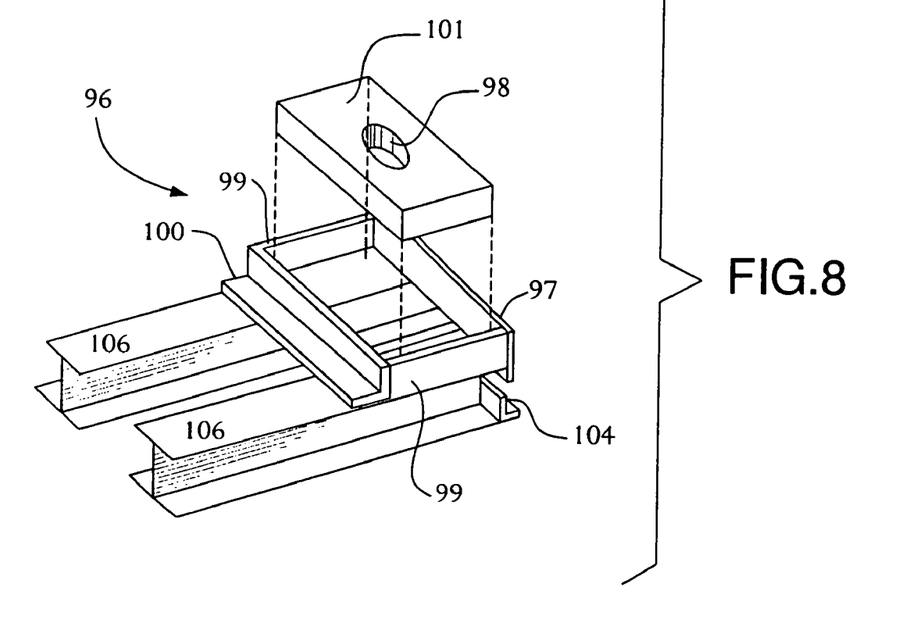
FIG. 8 is a detail perspective view of a rod-centering box component part of the present invention shown in elevation on FIG. 3.

Referring now to FIGS. 3, 4, and 8, each of the beam assemblies 115 and 116 is constructed of two parallel I-beams, with one rod centering box 96 at each end of each assembly 115 and 116. A detail of the rod centering box 96 is shown in FIG. 8, a perspective view of rod centering box 96.

One box 96 is welded at each end of each beam assembly 115 and 116. The boxes 96 are made of plates 99 welded to the top flanges 105 and 106 of the beam assembly 116 and 115, respectively, and of L-shaped bars 100, also welded to the flanges 105 and 106, respectively. The rod centering boxes 96 are completed by plates 97, also welded to flanges 105 and 106 respectively. The plates 99 are also welded to the angled bars 100 and to the plates 97. Angled bars 104 are welded to each end of the I-beams 115 and 116, respectively. With one rod centering box 96, and one angled bar 104 welded to each end of each pair of I-beams, very strong, novel reaction frames, i.e., beam assemblies 115 and 116, are formed. Support plates 101, shown lifted-up from box 96 in FIG. 8 are utilized to receive threaded rods 102 of the reaction anchor and support assemblies 125. Nuts 103 in FIGS. 3 and 4 are threaded onto the rods 102 and tightened against the support plates 101. The plates 101 can slide inside their respective centering box 96 to facilitate positioning the beam assemblies 115 and 116 over rods 102.

Figure 7:
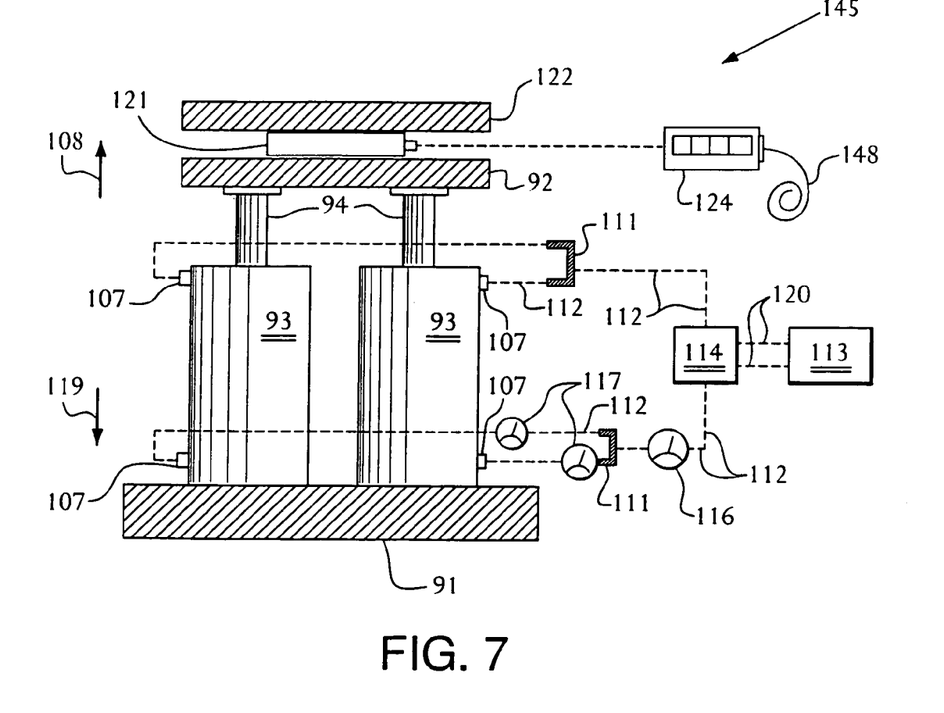
FIG. 7 is a detail elevation view of a hydraulic system component part of the present invention, also showing a load cell and a read-out with a graph print out.

Referring now to FIGS. 3 and 7, the hydraulic assembly 145 is shown set upon the test plate 91. The test plate 91 is set on top of the pile 90, which is the pile under test, as shown in FIG. 3.

To test the pile 90 for determining its capability of supporting its design load, a compressive load is axially applied upon the longitudinal axis of the pile 90, the compressive load being provided by the hydraulic assembly 145.

The pistons 94 of the hydraulic assembly 145 forcefully push, upwardly, against the bearing plate 92. This upward push of the pistons 94 is transmitted to the beam assemblies 115 and 116. Since the beam assemblies 115 and 116 are anchored by the reaction anchor and support assemblies 125, the beam assemblies 115 and 116 cannot move upwardly. The forceful upward push of the pistons 94, as they are forced out of their respective cylinders 93, is actually exerted axially, downwardly upon the pile 90, by means of the bottoms of the cylinders 93, upon the bearing plate 91.

Referring to FIG. 3, a pair of dial gages 109 have their stems 118 connected to a top surface 191 of the bearing plate 91 and to a pair of reference beams 110 by means of a pair of supports 147. The stems 118 must have, at a minimum, two inches (5 cm) of travel, must have a precision of at least 0.01 inches (0.25 millimeters) and must read to one sixty-fourth (1/64) of an inch (4 mm).

The dial gages 109 provide the measurement of any longitudinal axial movement of the pile 90 under the axial loading provided by the hydraulic assembly 145. Any axial movement beyond that specified renders the pile 90 unacceptable for its specified load.

Referring to FIGS. 3 and 6, the hydraulic assembly utilized in the apparatus and the method of the present invention could include a single hydraulic cylinder with its piston or a pair of cylinders 93 of a hydraulic assembly 95 of FIG. 6, with a pair of pressure gages 117, one pressure gage 117 for each hydraulic cylinder 93 and a master pressure gage 116, and further includes a hydraulic pump 113 and an automatic pressure control device 114. The cylinders 93 are connected to the pump 113 by a pair of common manifolds 111 and hoses 112. The complete hydraulic assembly 95 is to be calibrated as a unit, including the hydraulic cylinders 93, the pistons 94, the pressure gages 117 and 116, the pump 113, and the automatic pressure control device 114.

FIG. 7 represents the preferred embodiment of the hydraulic means utilized by the apparatus and the methods of the present invention. The hydraulic assembly 145 is very similar to the hydraulic assembly 95. Nevertheless, the hydraulic assembly 145 utilizes a calibrated load cell 121 between the bearing plate 92 and the bearing plate 122. In accord with the apparatus and the methods of the present invention, the calibrated load cell 121 is connected to a read-out and load graph recorder 124. The read-out recorder 124 provides a graph 148 showing the load applied during a 24-hour period. The calibrated load cell 121 and the read-out and load graph recorder 124 substantially improve the accuracy and reliability of the measurements of the loads applied to the pile-under-test 90. The preferred embodiment for the hydraulic means, e.g., the hydraulic assembly 145, also includes the pressure gages 117, one for each hydraulic cylinder 93 and the master pressure gage 116, the hydraulic pump 113, and the automatic pressure control 114. The cylinders 93 are connected to the pump 113 by the common manifolds 111 and the hoses 112. This apparatus and method provide a dual measuring system. The load cell 121 must be calibrated to an accuracy of not less than 2% of the applied load.

Referring again to FIG. 3, the reaction anchor and support assemblies 125, also referred to as anchor assemblies 125, are shown inside earthen holes 126. The reaction anchor and support assemblies 125 include anchoring heads 133 and a pipe column 128, which has four fins 129, only three shown, welded longitudinally to the surface of pipe column 128 and at ninety degrees to each other. The pipe columns 128 also have top plates 130 welded to their tops, which have a center hole to allow Dywidag Rod 102 pass through it, with a minimum clearance, in order to allow Dywidag nuts 132 to be tightened against the plates 130 when threaded down on the Dywidag rods 102. The Dywidag rods, the nuts, and other Dywidag products are manufactured by DywidagSystems International, U.S.A., Inc., of Fairfield, N. Jersey.

The anchoring heads 133 have the Dywidag rods 125 and a plate support 138 formed by four ninety-degree bars, only two being shown, with a plate 137 welded on their top and four compaction and consolidation pivoting plates 139, only three being shown. A collar 135 is welded on top of the plate 137 and is utilized to insert end 134 of the pipe column 128 into the collar 135 or over the collar 135, depending on pipe sizes utilized. Four bolts 136, only three shown, are utilized for firmly securing the pipe column 128 to the anchor head 133. The Dywidag rod 102 is inserted through a centerhole in a frusto-cone 140. A Dywidag nut 141 is threaded on the end of the rod 102 and prevents the frusto-cone 140 from falling down.

A nut 168 is hand tightened on the Dywidag rod 102, on top of the frusto-cone 140, as seen in FIG. 4. The main purpose of the nut 141 is to carry the frusto-cone 140 upwardly whenever the rod 102 is pulled up, during the process of anchoring the reaction anchor and support assembly 125, prior to installing the test beam assemblies 115 and 116.

During the installation of the reaction anchor and support assemblies 125, hydraulic force is utilized for pulling up on the rod 102. The pulling on the rod 102 forces the nut 141 to push the frusto-cone 140 upwardly, which in turn pushes the compaction and consolidation pivoting plates 139 upwardly and outwardly. The pulling on the rod 102 makes the pivoting plates 139 swing upwardly and outwardly, thereby compacting and consolidating soil 127 at the bottom of the earthen hole 126, effectively anchoring the assembly 125 against the soil 127 at the bottom of the earthen hole 126, thus providing the reaction point needed for the pile test. A nut 132 is threaded downwardly and hand tightened against the plate 130 at the top of the pipe column 128 in order to prevent the rod 102 and the frusto-cone 140 from moving back down.

The top end of the reaction anchor and support assembly 125 is left a few inches above grade in order to facilitate its retrieval for further use. Holes 131 are utilized for hooking a lifting device.

The reaction anchor and support assemblies 125 are installed at a distance of at least seven feet, clear distance, from the pile 90.

The pile 90 of FIG. 3 is shown as a round, cylindrical pile. Nevertheless, the pile 90 can be an H-pile, an L-pile, a square pile, or an orthogonal pile. The pile 90 can be a concrete pile, whether cast-in-place or pre-cast, a pipe pile, or a timber pile, by the way of an example.

The test set up shown in FIG. 3 requires four reaction anchor and support assemblies 125, as shown in FIG. 4, in order to provide an anchored reaction capacity, which is greater than the axial load applied to the pile 90 by the hydraulic assembly 145. The axial loading or test loading required for testing single piles is at least 200% of the pile design load capacity. Nevertheless, smaller piles require smaller test loads, and only one pair of reaction anchor and support assemblies 125 are required for smaller piles.

On occasion, three pairs of reaction anchor and support assemblies 125 are required. In such cases, an additional beam assembly is installed upon the beam assembly 115 and at fortyfive degrees from it. The additional pair of reaction anchor and support assemblies are installed as shown for the beam assemblies 115 and 116 and in a substantially similar manner as shown for the reaction anchor and support assemblies 125 of FIGS. 3 and 4.

Figure 5:
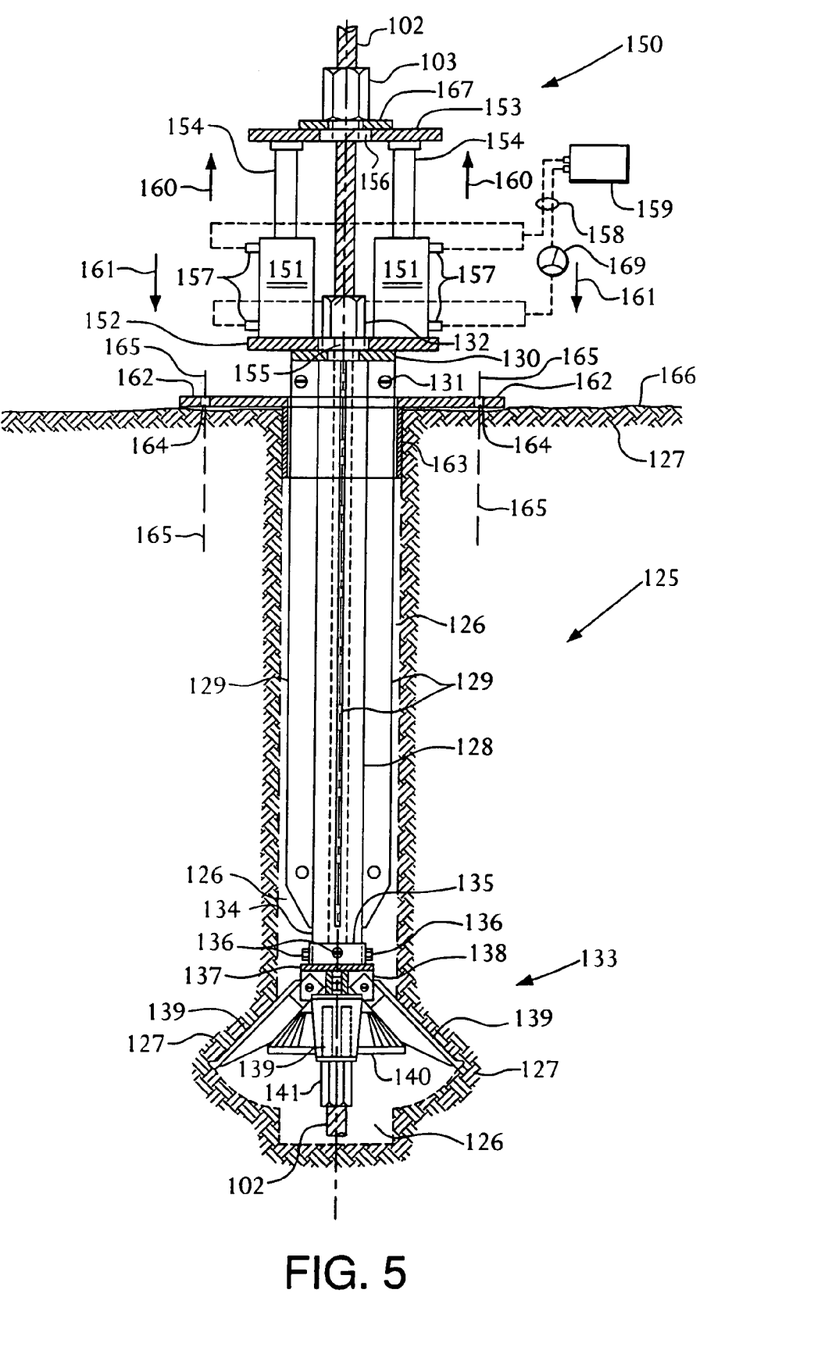
FIG. 5 is an elevation view, partially in section, of a reaction anchor and support assembly in accordance with the apparatus and methods of the present invention.
Figure 9:
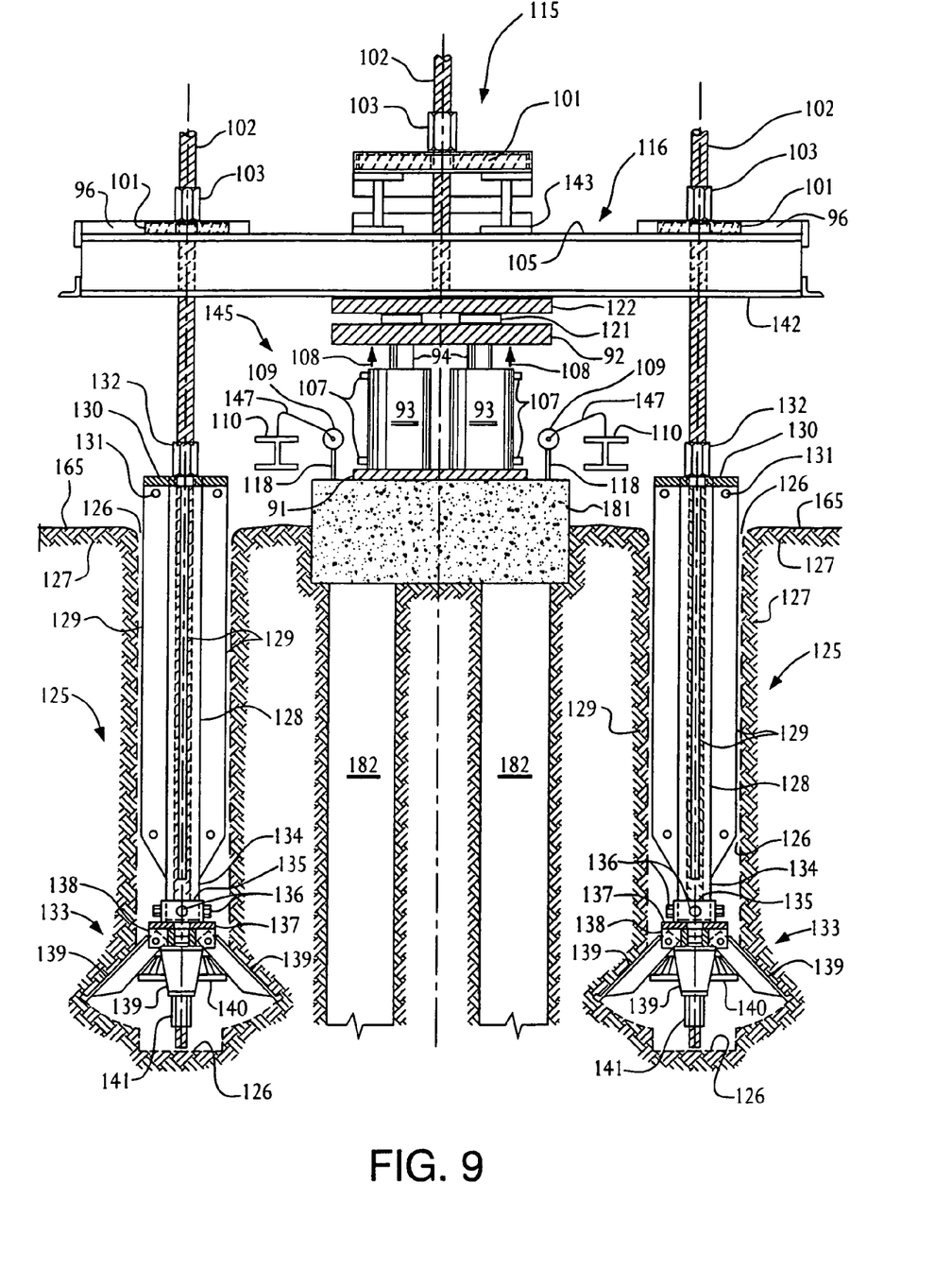
FIG. 9 is an elevation view, partially in section, showing a pile group testing apparatus of the present invention, utilizing a concrete pile cap.

Referring now to FIG. 5, one reaction anchoring and support assembly is shown of the four reaction anchoring and support assemblies of FIGS. 3, 4, and 9. The one reaction anchoring and support assembly is shown in the process of being installed inside a pre-augured earthen hole 126, in preparation for utilization in the testing of the single pile 90 of FIG. 3 or group pile 180 of FIG. 9.

The reaction anchor and support assembly 125 of FIG. 5 provides the anchored reaction capacity required to resist the upward push of the hydraulic assemblies 145 of FIGS. 3, 4, and 9. The upward push of the hydraulic assemblies 145 provides the resultant downward axial loading required for testing the single pile 90 of FIG. 3 or the group pile 180 of FIG. 9.

The reaction anchor and support assemblies 125 are brought to the test site in one piece, pre-assembled, with the anchoring head 133 pre-attached to the rod 102 and with the rod 102 inside the pipe column 128. The compaction and consolidation pivoting plates 139 come to the test site vertically down and parallel to the rod 102, with the frusto-cone 140 below the tip end of the compaction and consolidation pivoting plates 139. The frusto-cone 140 is sandwiched between the nut 168, on its topside, as shown in FIG. 4 and the nut 141 on its bottom side as shown in FIG. 5. The pivoting plates 139 come with breakable tie-wire (not shown) around them, in order to keep them in a vertical position, which facilitates lowering down the anchor assembly 125 inside the pre-augured earthen hole 126. The nut 132 comes to the test site hand tightened against the plate 130.

The reaction anchor and support assembly 125 is lowered down inside the earthen hole 126. About six inches of the top end of the reaction anchor and support assembly 125 is left above ground level 166. A centering collar 163 is placed over the assembly 125 and pushed down inside the earthen hole 126, until its plate 162 rests on surface 166 of the soil 126. The collar 163 is about twelve to eighteen inches long. The centering collar 163 is utilized for centering the reaction anchor assembly 125 inside the earthen hole 126 and to make sure it is fixed in a true, vertical and leveled position. When the correct leveling is attained, four pins 165 (only two are shown) are hammered down into the soil 127, through holes 164 of the plate 162, in order to immobilize the centering collar in a vertical position.

Next, the hydraulic assembly 150 is placed over the rod 102, i.e., with the rod 102 passing through openings 155 and 156 on plates 152 and 153, respectively. This is done by means of a crane, which is available at the job site anyways for handling the piles. The hydraulic assembly 145 of FIG. 7 could be utilized instead of the hydraulic assembly 150 of FIG. 5, if plates 91, 92, 94, and the load cell 121 had an opening through their center, for allowing the rod 102 pass through it.

The preferred embodiment provides for utilizing one single hydraulic assembly to perform both the installation of all the reaction anchor and support assemblies 125 prior to testing, as well as providing the specified loading for testing the single pile 90 of FIG. 3 or the pile group 180 of FIG. 9. In such an embodiment, the load cell 121 also has a center hole. If the load cell 121 also is utilized for installing the anchor assembly 125, then it could be installed between the plate 91 of FIG. 7 and the plate 130 of FIG. 5. The utilization of the load cell 121 and the read-out/graph recorder 124 is not a requirement for the installation of the reaction anchoring and support assemblies 125. Nevertheless, the utilization of the load cell 121 and the read-out/graph recorder 124 is an additional quality control feature as well as a record keeping feature and a component part of the present invention.

When the hydraulic assembly 150 is set on top of the plate 130, a plate 167 is placed over the rod 102 and set on top of the plate 153 to reduce the actual size of opening 156 so that the Dywidag nut 103 can be threaded down on the rod 102 and hand tightened against the plates 167 and 153.

The hydraulic assembly 150 has cylinders 151 connected by means of hoses 158 through the assembly's inlets 157 to a hydraulic pump 159. A master pressure gage 168 is provided in series with both the cylinders 151 and the pump 159. A pressure gage 169 provides a reading of the pressures applied by the pistons 154, in pounds per-square inch, p.s.i. The total force exerted by the assembly is directly proportional to the diameter of pistons 154. The diameter of the pistons 154 determines the area in square inches of the cross section of each piston 154, which pistons 154 are substantially identical pistons. Therefore, the total combined area is determined in advance.

The operator is provided with a simple table showing how many tons-force are equivalent to various p.s.i. readings from the gage 169. The operator does not calculate anything. The compaction and consolidation pivoting plates 139 are at the bottom of the earthen hole 126 in a vertical position parallel to the rod 102. The next step is to swing upwardly the pivoting plates 139 to anchor the assembly firmly against the soil 127 at the bottom of the hole 126.

The operator provides hydraulic pressure to the cylinder 151, through the bottom inlets 157, which forces the pistons 154 upwardly. The pistons 154 forcefully push against the plates 153, 167 and the nut 103. That forceful upward push as represented by arrows 160 and as exerted on the nut 103, which is threaded onto the rod 102, lifts the rod 102 up, which in turn carries the nut 141 up with it. The nut 141 is threaded to the bottom end of the rod 102. The nut 141 pushes up the frusto-cone 140, which in turn forces the pivoting plates 139 to break their tie-wire (not shown). The pivoting plates 139 are forced to swing upwardly, compacting and consolidating the soil 127 at the bottom of the hole 126 by the expanding plates, i.e., by the expansion of the pivoting plates 139, thereby powerfully anchoring assembly the 125 to the soil at the bottom of the hole 126. As the rod 102 is being slowly, yet powerfully pushed upwardly, the operator hand-tightens down the nut 132 against the plate 130, thereby preventing the pivoting plates 139 from collapsing back down, which is a very rear situation.

Now the hydraulic assembly 150 is removed, by first reversing the flow of hydraulic fluid, which now is pumped by the pump 159, through the upper inlets 157, which in turn brings the pistons 154 back inside of their respective cylinders 151. Then the hydraulic pressure is released and the nut 103 and the plate 167 are removed. Finally, the hydraulic assembly 150 is removed and the installation of the next anchoring assemblies 125 can be started, until all four assemblies required per FIGS. 3, 4 and 9 are installed.

Preferably, the centering collar 163 stays installed, one on each anchoring assembly 125 until the pile test is concluded and the anchoring assemblies 125 are removed.

As opposed to the conventional methods, whereby the anchor piles utilized in the testing remain in the ground and their tops must be sawed off, the reaction anchoring and support assemblies 125 are reusable.

The anchoring and support assemblies 125 are retrievable. They are retrieved from the earthen hole 126 utilizing the same hydraulic assembly they were installed with.

In order to retrieve the reaction anchor and support assemblies 125 from the earthen hole 126, after the pile testing is completed, first the operator places the hydraulic assembly 150 once more over the rod 102, by means of an on-site crane. Then the operator lowers the assembly down so that the rod 102 passes through the hole 155 on the bottom plate 152 and through the hole 156 of the top plate 153. Now, the plate 167 is reinstalled, and the nut 103 is rethreaded down on the rod 102 and hand tightened against the plate 167.

The operator then pumps hydraulic fluid through the lower inlets 157, by means of the pump 159. This forces the pistons 154 out of their respective cylinders 151, slowly but forcefully pushing upwardly against the plates 153 and 167 and on the nut 103 which, being threaded onto the rod 102, slowly lifts the rod 102 upwardly. This is done just enough to release the enormous pressure exerted by the nut 132 against the plate 130 at the time the anchor and support assembly 125 was installed. Now the operator threads the nut 132 upwardly on the rod 102 and then releases the pressure from the pump 159, which releases the upward push of the pistons 154.

Next the nut 103 and the plate 167 are removed, and the operator pumps again hydraulic fluid through the lower inlets 157, by means of the pump 159, to make the pistons 154 extend out of the cylinders 151 for a distance which is approximately equal to the distance the pistons 154 were extended during the process of installation. The hydraulic assembly then is lifted up again, by means of a crane, just enough, so that the top end of the rod 102 is below the plate 153, in order to allow re-introducing the plate 167, which now will be on top of the nut 132, which has been threaded up.

Then, the operator lowers down the hydraulic assembly and sets its bottom plate 152 back on top of the plate 130 of the reaction anchor and support assembly 125 and with the rod 102 passing through the hole 156 of the top plate 153.

The operator further threads up the nut 132 carrying the plate 167 upwardly until the plate 167 is against the bottom of the plate 153 with the nut 132 hand-tightened under it.

Now the operator pumps hydraulic fluid through the upper inlets 157, which forces the pistons 153 back down, slowly but forcefully pushing downwardly on the nut 132, which now is under the plates 167, 153 and is threaded onto the rod 102. Therefore the pistons 154, slowly yet powerfully, push the rod 102 down. Since the nut 168, shown on FIG. 4, is threaded onto the rod 102 and it is on top and in contact with the frusto-cone 140, it pushes the frusto-cone 140 also downwardly. By pushing the frusto-cone 140 downwardly, the compaction and consolidation pivoting plates 139 are effectively released from the powerful force which kept them pressed against the soil at the bottom of the earthen hole 126.

With the pivoting plates 139 collapsed back down to a vertical position, now the hydraulic assembly can be finally removed, as previously described, after releasing the hydraulic pressure.

A job-site crane then is utilized for lifting the anchor and support assembly 125 out of the earthen hole 126. Openings 131 on fins 129 are utilized for helping in lifting the assembly by means of devises and the job-site crane.

Referring now to FIG. 9, the reaction anchor and support assemblies 125, utilized by the methods of the present invention, are shown in the process of testing a pile group 180 under a static axial load provided by the hydraulic assembly 145.

The pile group 180 includes two or more single piles 182. The pile group 180 is capped with a reinforced concrete cap 181 engineered and constructed specifically for the anticipated test loads.

The hydraulic cylinders 93 are set on the bearing plate 91, with their respective pistons 94, upon which the bearing plate 92 is set. The load cell 121 is set in between the bearing plate 92 and the bearing plate 122. The bearing plates 91, 92 and 122 are of sufficient thickness to support the test loads provided by the hydraulic assembly 145 without bending, but not less than two inches thick.

The plate 122 bears against the flange 142 of I-beam assembly 116. The I-beam assembly 116 bears against the I-beam assembly 115, which is identical to the beam assembly 116. The flanges 143 of the I-beam assembly 115 are set on top of the flanges 105 of I-beam assembly 116. The beam assembly 115 is set at ninety degrees of the beam assembly 116 in the horizontal plane and on top of it.

The construction of the I-beam assemblies 115 and 116 of FIG. 9 is substantially the same as described in reference to FIGS. 3 and 4. The hydraulic assembly 145 of FIG. 9 also is substantially the same as described in reference to FIGS. 3 and 7. Nevertheless, for the pile group 180 testings, a larger axial load is required, for a larger capacity for the hydraulic cylinders 93, with their respective pistons 94, possibly, of larger diameter than it would be required for single pile testings.

The reaction anchor and support assemblies 125 of FIG. 9 are also substantially the same as described in reference to FIGS. 3, 4 and 5. On occasion, a third pair of assemblies 125 is utilized in order to provide the reaction capacity required for the loading specified for a specific pile group test.

Continuing to refer to FIG. 9, the instrumentation set up is substantially similar to that described in reference to FIG. 3. Nevertheless, for the group pile testing of FIG. 9, the dial gages 109 have their stems 118 connected to the top of the concrete cap. The dial gages 109 are connected to reference the beams 110 by means of the supports 147. The stems 118 must have, at a minimum, two inches (5 Cm) of travel, must have a precision of at least 0.01 inches (0.25 millimeters) and must read to one sixty-fourth (1/64) of an inch. These dial gages provide the measurement of any longitudinal axial movement of the pile group 180 under the axial load provided by the hydraulic assembly 145. Any axial movement beyond that specified, renders pile 90 unacceptable for its specified load.

Other instrumentation means are available for measuring other single pile and group pile movements under axial test loadings.

By the novel methods of the present invention, single piles or group piles are tested utilizing one, two, or more pairs of reaction anchor and support assemblies, as shown in FIGS. 3, 4, and 9 and as described in the detailed description, instead of utilizing one, two, or more pairs of anchor piles which cannot be reutilized for future pile or pile group tests.

The testing process of the present invention does not depart from the procedures established by the A.S.T.M. standards for testing piles or pile groups. The novelty of this invention includes the utilization of the novel anchor and reaction anchoring and support assembly in combination with the novel I-beam assembly, with a built-in centering box. This combination, in addition to its reusability feature, is a safer and more reliable anchoring system than the conventional anchor piles utilized by the conventional methods. The mechanical connections between the conventional reaction beam and the conventional anchor piles of the conventional methods are substantially more susceptible to elongation under the axial pressures involved in the test than the Dywidag rod and Dywidag nuts combination utilized by this invention.

The component parts of the reaction anchor and support assembly of this invention have been utilized under axial loadings several times larger than the loads involved in pile tests.

The safety and reliability of the methods of this invention are demonstrated further by the anchoring method of this invention, which compacts and consolidates the soil it is anchored to, with the compaction and consolidation increasing, thus increasing the anchoring capacity, as the test loading increases. This can be understood readily by looking at the drawings in FIGS. 3, 5, and 9, showing the swingable pivoting plates anchored and pushing upwardly, at the bottom of an earthen hole, such that the more the test load pulls up on the Dywidag rod, the more powerfully the anchoring head gets anchored to the soil at the bottom of the hole.

The apparatus and method of the present invention substantially contrast with the conventional anchor piles, which depend absolutely on the friction between the pile and the soil into which it was hammered down. In the conventional application, the more the test load pulls the anchor pile up, the greater are the chances the pile will slide up, and often the piles do slide up.

As it can be seen by a review of the detailed description, the apparatus and method of the present invention accomplish all of its stated objectives. The apparatus and methods of the present invention are capable of modifications and variations without departing from the scope thereof. Accordingly, the detailed description and examples set forth above are meant to be illustrative only and are not intended to limit the scope of the invention as set forth in the appended claims.

What is claimed is:

1. Pile testing apparatus for testing load bearing capacity, comprising:
   a. means for applying a static compressive force on a pile to be tested for load bearing capacity;
   b. an I-bean adapted to receive a reaction force opposite of said compressive force on said pile to be tested;
   c. two retractable and reusable reaction anchor assemblies positioned in the ground on opposite sides of said pile to be tested, wherein said reaction anchor assemblies are easily retractable from the ground and reusable; and
   d. means for bracing said I-beam by said two retractable and reusable reaction anchor assemblies to hold said I-beam stationary in counter-action against said opposite reaction force on said I-beam,
   wherein each of said retractable and reusable reaction anchor assemblies has an anchoring head, a pipe column, a center, and a pulling rod passing through said center.

2. Pile testing apparatus for testing load bearing capacity, comprising:
   a. means for applying a static compressive force on a pile to be tested for load bearing capacity;
   b. an I-bean adapted to receive a reaction force opposite of said compressive force on said pile to be tested;
   c. two retractable and reusable reaction anchor assemblies positioned in the ground on opposite sides of said pile to be tested, wherein said reaction anchor assemblies are easily retractable from the around and reusable; and
   d. means for bracing said I-beam by said two retractable and reusable reaction anchor assemblies to hold said I-beam stationary in counter-action against said opposite reaction force on said I-beam,
   wherein each of said retractable and reusable reaction anchor assemblies has an anchoring head, a pipe column, and four fins welded longitudinally along said pipe column.

3. The pile testing apparatus for testing load bearing capacity as set forth in claim 1, wherein each of said retractable and reusable reaction anchor assemblies further comprises at least one swingable anchoring plate actuated by said pulling rod.

4. The pile testing apparatus for testing load bearing capacity as set forth in claim 3, further comprising a frusto-cone for pivoting said swingable anchoring plates.

5. A method of testing piles for load bearing capacity, comprising:
   a. applying a static compressive force on a pile to be tested for load bearing capacity;
   b. applying an opposite reaction force on an I-beam;
   c. providing two retractable and reusable reaction anchor assemblies on opposite sides of said pile; and
   d. bracing said I-beam by said two retractable and reusable reaction anchor assemblies to hold said I-beam stationary in counter-action against said opposite reaction force on said I-beam,
   wherein each of said retractable and reusable reaction anchor assemblies has an anchoring head, a pipe column, and four fins welded longitudinally alone said pipe column.

6. The method of testing piles for load bearing capacity as set forth in claim 5, further comprising applying a compressive force against a group of piles to be tested for load bearing capacity.

7. The method of testing piles for load bearing capacity as set forth in claim 5, wherein each of said retractable and reusable reaction anchor assemblies has an anchoring head, a pipe column, a center, and a pulling rod passing through said center.

8. A method of testing piles for load bearing capacity comprising:
   a. applying a static compressive force on a pile to be tested for load bearing capacity;
   b. applying an opposite reaction force on an I-beam;
   c. providing two retractable and reusable reaction anchor assemblies on opposite sides of said pile, wherein each of said retractable and reusable reaction anchor assemblies has an anchoring head, a pipe column, and four fins welded longitudinally along said pipe column; and
   d. bracing said I-beam by said two retractable and reusable reaction anchor assemblies to hold said I-beam stationary in counter-action against said opposite reaction force on said I-beam,
   wherein each of said retractable and reusable reaction anchor assemblies has an anchoring head, a pipe column, a center, and a pulling rod passing through said center, and
   wherein each of said retractable and reusable reaction anchor assemblies further comprise at least one swingable anchoring plate actuated by said pulling rod.

9. The method of testing piles for load bearing capacity as set forth in claim 8, comprising a pair of said swingable anchoring plates.

10. The method of testing piles for load bearing capacity as set forth in claim 9, comprising four retractable and reusable reaction anchor assemblies.

11. The method of testing piles for load bearing capacity as set forth in claim 9, comprising six retractable and reusable reaction anchor assemblies.

12. The method of testing piles for load bearing capacity as set forth in claim 9, wherein said anchoring head, said pipe column, and said pulling rod are preassembled for transportation to a pile test site.

13. The method of testing piles for load bearing capacity as set forth in claim 9, further comprising a frusto-cone for pivoting said swingable anchoring pleates.

14. The method of testing piles for load bearing capacity as set forth in claim 9, further comprising reusing said reaction anchor assemblies from one pile test site to another.

15. The method of testing piles for load bearing capacity as set forth in claim 9, comprising retrieving said reaction anchor assemblies from the ground after completion of the pile test.

* * * * *

UNITED STATES PATENT AND TRADEMARK OFFICE
CERTIFICATE OF CORRECTION

PATENT NO. : 7,347,103 B2 Page 1 of 1
APPLICATION NO. : 11/266978
DATED : March 25, 2008
INVENTOR(S) : Reinert, Sr.

It is certified that error appears in the above-identified patent and that said Letters Patent is hereby corrected as shown below:

Column 13, line 59, Claim 5, "alone" should read -- along --

Column 14, line 51, Claim 13, "pleates" should read -- plates --

Signed and Sealed this

Nineteenth Day of August, 2008

JON W. DUDAS
*Director of the United States Patent and Trademark Office*